United States Patent [19]

Nelson

[11] Patent Number: 4,797,614
[45] Date of Patent: Jan. 10, 1989

[54] APPARATUS AND METHOD FOR MEASURING CONDUCTANCE INCLUDING A TEMPERATURE CONTROLLED RESONANT TANK CIRCUIT WITH SHIELDING

[75] Inventor: Roger E. Nelson, Northridge, Calif.
[73] Assignee: Sierracin Corporation, Sylmar, Calif.
[21] Appl. No.: 45,244
[22] Filed: Apr. 20, 1987

Related U.S. Application Data

[63] Continuation of Ser. No. 667,537, Dec. 3, 1984, abandoned.

[51] Int. Cl.$^4$ .................... G01R 27/00; G01N 27/72; H03B 1/00; H01F 15/04
[52] U.S. Cl. .................................. 324/236; 324/62; 324/158 R; 324/224; 331/65; 331/67; 331/70; 336/55; 336/84 R
[58] Field of Search ............... 324/158 R, 158 D, 224, 324/225, 230, 236, 237, 327, 328, 62, 65 R, 65 P, 57 Q, 61 QS; 331/65–67, 69, 70; 336/55, 84 R, 84 C, 84 M; 343/841, 842

[56] References Cited

U.S. PATENT DOCUMENTS

| | | | |
|---|---|---|---|
| 2,047,159 | 7/1936 | Wood et al. | 336/84 C X |
| 2,859,407 | 11/1958 | Henisch | 324/158 |
| 2,920,268 | 1/1960 | Young | 324/230 X |
| 3,234,461 | 2/1966 | Trent et al. | 324/62 |
| 3,252,084 | 5/1966 | Krobath | 324/224 |
| 3,409,805 | 11/1968 | Whipple et al. | 336/84 C X |
| 3,444,460 | 5/1969 | Penney | 324/260 |
| 3,473,110 | 10/1969 | Hardin et al. | 324/236 |
| 3,519,919 | 7/1970 | Rance | 324/328 |
| 3,544,893 | 12/1970 | Savin et al. | 324/62 |
| 3,651,398 | 3/1972 | Urmenyl | 324/224 |
| 3,805,160 | 4/1974 | Philbrick et al. | 324/158 D |
| 3,833,850 | 9/1974 | Weber | 324/236 |
| 3,939,403 | 2/1976 | Stassart | 324/224 |
| 4,000,458 | 12/1976 | Miller et al. | 324/34 R |
| 4,105,105 | 8/1978 | Braum | 324/236 X |
| 4,220,915 | 9/1980 | Kawamoto et al. | 324/58 A |
| 4,343,027 | 10/1982 | Ballato et al. | 324/56 |
| 4,451,812 | 5/1984 | Vescovi et al. | 336/84 C |
| 4,564,810 | 1/1986 | Geithman et al. | 324/230 |

FOREIGN PATENT DOCUMENTS

| | | | |
|---|---|---|---|
| 0021363 | 2/1979 | Japan | 324/224 |
| 153787 | 7/1963 | U.S.S.R. | 324/224 |

OTHER PUBLICATIONS

"Non-Contact Resistivity Meter", *Circuits Manufacturing,* Apr. 1976, p. 64.
"The Sound of Thickness", by Barry Hart, *Industrial Research/Development,* May, 1979, pp. 129–131.
"m-gage 200 Metalization Monitor" Brochure, Tencor Instruments, Aug. 1983.

*Primary Examiner*—Gerard R. Strecker
*Attorney, Agent, or Firm*—Sheldon & Mak

[57] ABSTRACT

A meter for sheet conductance measurements does not touch the conductive surface of a sample. A probe having a resonant tank coil is positioned against a parallel supporting surface of the sample, which may be flat or curved and of unrestricted area. An oscillator incorporating the tank coil is controlled to stabilize oscillator amplitude in response to eddy current loading by the sample. An electrostatic shield in a finger configuration prevents capacitive coupling between the tank coil and the sample without hindering magnetic coupling. A readout of sheet conductance is driven by the oscillator control. Direct current can be coupled to the tank coil for temperature control preventing undesired resistance changes in the tank coil. The oscillator can be controlled by an optically coupled variable gain element. Measurements can be made with the tank coil up to at least 0.75 inch from the conductive surface of the sample.

11 Claims, 3 Drawing Sheets

APPARATUS AND METHOD FOR MEASURING CONDUCTANCE INCLUDING A TEMPERATURE CONTROLLED RESONANT TANK CIRCUIT WITH SHIELDING

This application is a continuation, of application Ser. No. 667,537, filed Dec. 3, 1984, abandoned.

BACKGROUND

This invention relates to electrical conductance measurements, and more particularly to noncontact sheet conductance measurements.

Non-contact conductance measurements based on the loading effects of a sample on the "Q" of a nearby coil are known in the prior art. Sheet conductance ($G_s$) in units of Siemens per unit square is the inverse of sheet resistance ($R_s$) in units of ohms per unit square.

The analyses of these loading effects are quite complex, involving the concepts of alternating magnetic fields, magnetic coupling, mutual inductance, vector descriptions of induced currents and their interactions with their associated magnetic fields. When concerned with the interactions of time varying magnetic fields on conductive or semi-conductive objects or surfaces, the subject is generally lumped into the concept of "eddy currents". Eddy currents are induced in the object by the magnetic field. The resulting losses and interactive magnetic field are reflected back into the driving inductor. These are seen as the changes in the resistive and inductive components of the impedance of the coil. The figure of merit Q is defined as the ratio of the reactive to the resistive impedance components of a coil at a given frequency. Thus the reflection of eddy current losses from a sample conductor to a coil influences the Q of the coil.

The change in Q depends on the conductivity of the sample and the proximity of the sample to the coil. The magnitude of the eddy current loading effect is very sensitive to the distance between the sensor coil and a conductive surface. Therefore, means must be provided to establish a definite positional relationship between the sensor and the conductive surface of a sample.

The prior art includes devices for determining resistivities by measurements of Q in combination with the use of non-linear calibration curves of resistivity versus Q from samples of known resistivity. For example, U.S. Pat. No. 3,234,461 to Trent et al discloses the use of a commercial Q meter connected to a slotted coil with calibration curves relating actual and relative Q to the resistivity of samples positioned within the slot.

The prior art also includes U.S. Pat. No. 4,000,458 to Miller et al, disclosing a method of measuring sheet conductance of a sample as a linear function of the drive current required in a constant amplitude resonant circuit loaded by the sample. The Miller patent describes a resonant coil tightly coupled to both sides of the sample and magnetically shielded by aluminum cups for confining the magnetic field to a defined area of the sample. An electrostatic shield of conductive paper covers open ends of the cups between the coil and the sample for minimizing capacitive coupling to the sample.

Prior art non-contact sheet conductance and bulk conductivity meters are commonly used for process control of semiconductor wafers and chips in the microelectronics industry.

Another application for sheet conductance measurements is in the process control of large area substrates having an applied conductive surface. These conductive surfaces are often quite delicate and must not be touched. The substrates can be panels spanning several feet and having thicknesses of up to ¾ inch (20 mm). The substrates can be made from a non-conductive material such as glass or plastic.

The term "non-contact" has been used in the prior art to distinguish from earlier prior art meter technology using a traditional four point probe to establish direct electrical contact with the conductive surface of the sample.

Usually, the sample is sandwiched in a slot within the coil or in a gap between portions of the core. Consequently, both sides of the sample are subject to being touched by the meter through normal handling procedures.

A successful commercial instrument identified as "M-gage 200" Metalization Monitor", manufactured by Tencor Instruments Company is designed specifically for semiconductor wafers. It provides for the positioning requirement by incorporating a transport mechanism to support the wafer and position it accurately between two sensor coils approximately ¼ inch apart. The sample wafers can have a maximum thickness of 0.120 inch.

A disadvantage of prior art non-contact conductivity meters is a requirement for close proximity (less than 0.15 inch) of the conductive surface to the sensor (a coil or a high permeability core tightly coupled to the coil). In order to provide for exact and repeatable spacing of the sensor to the sample, prior art meters usually compromise the non-contact feature by requiring physical contact of some part of the sensor assembly with the conductive surface of the sample in order to establish the required exact spacing between the sensor and the sample.

A noncontact resistivity meter touching one side only of the sample is disclosed in U.S. Pat. No. 2,859,407 to Henisch. For samples comprising a conductive material on a thick substrate, the conductive surface must face the meter to be in close proximity to the coil for proper meter operation. Therefore, unless the sample is very thin, the meter must touch the conductive surface of the sample.

A further application for sheet conductance measurements is in the manufacturing of panels having a conductive surface between thick laminated substrates, such as for windshields. These panels are sometimes curved. The prior art resistance meters are not suitable for this application because the internal conductive surface cannot be in close proximity to the coil.

A problem encountered in locating the conductive surface a distance from the instrument is that an interposed conductive surface used as an electrostatic shield, as described above, interferes with magnetic coupling to the sample. The more remotely the sample is located from the coil and the shield, the more dominantly the shield loads the resonant circuit, rendering the instrument insensitive to the conductivity of the sample.

Another disadvantage of prior art non-contact sheet conductance and bulk conductivity meters is that they are not suitable for measurements of large samples. The non-contact meters of the prior art require samples for measurement to be placed within or on the instrument. This would be quite cumbersome, even for measurements near the edge of the sample. Measurements remote from the edge of the sample would require destructive cutting of the sample.

Thus there is a need for a noncontact sheet conductance meter that can be conveniently used on large area flat or curved samples having a variety of thicknesses and having interior or exterior conductive surfaces that must not or cannot be touched by the meter.

SUMMARY

The meter of the present invention meets these needs by providing an eddy current probe for use against a supporting surface of the sample that can be at a substantial predetermined distance from the conductive surface.

The meter comprises a tank coil used as an inductive element in a tank circuit, the coil being positioned at a predetermined distance from the sample, the tank circuit being connected in an oscillator amplifier circuit, the oscillator amplifier circuit being controlled in response to eddy current loading of the tank coil by the sample, a control voltage being produced proportional to sheet conductivity of the sample. The tank coil is capacitively shielded from the sample by a plurality of separate conducting fingers for preventing eddy current losses in the shield. The difference between the control voltage and an adjustable offset voltage can be amplified by an output amplifier and displayed by a digital voltmeter as the sheet conductance of the sample.

Preferably the tank coil is in a probe remote from an electronics package housing the control electronics. The probe is constructed for convenient alignment of the tank coil perpendicular to the supporting surface at a predetermined distance from the sample, which surface can be flat or uniformly curved parallel to the conductance surface. Preferably the probe is remotely connected to the electronics package by a coaxial cable more than two feet long for convenient manipulation of the tank coil.

Preferably the oscillator comprises a high frequency operational amplifier with optically coupled gain control driven by the control signal.

Preferably means are provided for controlling the temperature of the tank coil to avoid changes in Q caused by the resistance of the tank coil changing with temperature. Direct current for heating is coupled to the tank coil. A control circuit varies the direct current in response to measured changes in the tank coil resistance for stabilizing the resistance and temperature of the tank coil. Preferably a divider circuit measures the tank coil resistance as a ratio of tank coil voltage to the corresponding direct current.

Preferably the probe is provided with a shield connected to the coaxial cable and surrounding the tank coil, the portion of the shield between the tank coil and the sample forming closely spaced long narrow conductors interconnected at one location only on each conductor. Preferably the conductors form two closely spaced surfaces, the conductors of each surface crossing at an angle of about ninety degrees. The interconnections of the conductors are electrically connected to a conductive housing completing an electrostatic shield for the coil. The conductive housing provides magnetic shielding for magnetic flux associated with the tank coil not directed toward the sample. The combination of the conductive housing and the conductors connected at one location only confines the magnetic field of the tank coil to an area of the sample substantially corresponding to an area only slightly larger than that circumscribed by the diameter of the housing, and electrostatically shields the tank coil from the sample without interfering with magnetic coupling between the tank coil and the sample.

The shield configuration of the probe permits meaningful sheet conductance measurements to be made at very high gain sensitivities so that, when necessary, the tank coil can be located a substantial distance of at least 0.75 inch from the conductive surface of the sample. In addition, the remotely connected probe can be conveniently positioned on a large sample to measure selected areas of a conductive surface without touching the conductive surface.

Thus a noncontact sheet conductance meter is provided that can measure the sheet conductance of selected areas within a large flat or curved panel having substantial thickness and having an interior or exterior conductive surface that must not or cannot be touched by the meter.

DRAWINGS

These and other features, aspects, and advantages of the present invention will become better understood with reference to the following description, appended claims, and accompanying drawings where:

DESCRIPTION

Figure 1:
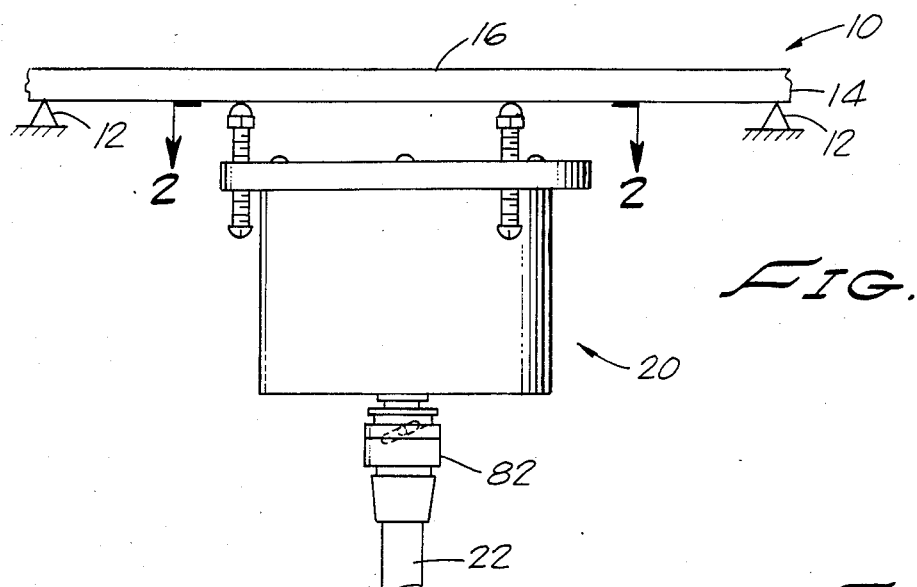
FIG. 1 is a fragmentary elevational view showing a probe of the meter of the present invention positioned against a supporting surface of a sample.

The present invention is directed to a noncontact sheet conductance meter that can be used on a variety of samples having conductive surfaces that must not or cannot be touched by the meter. With reference to FIG. 1, a conductive sheet or sample 10 rests on a support 12. The sample 10 comprises a subsrate 14 having a conducting surface 16 and an opposite supporting surface 18, the supporting surface 18 being in contact with the support 12. A probe 20 is positioned against the supporting surface 18 for measurement of the conductivity of the conducting surface 16 of the sample 10. Although shown beneath the sample 10 for illustrative purposes, the probe 20 can be used in any position to provide convenient proximity to the sample.

Measurement Electronics

Figure 4:
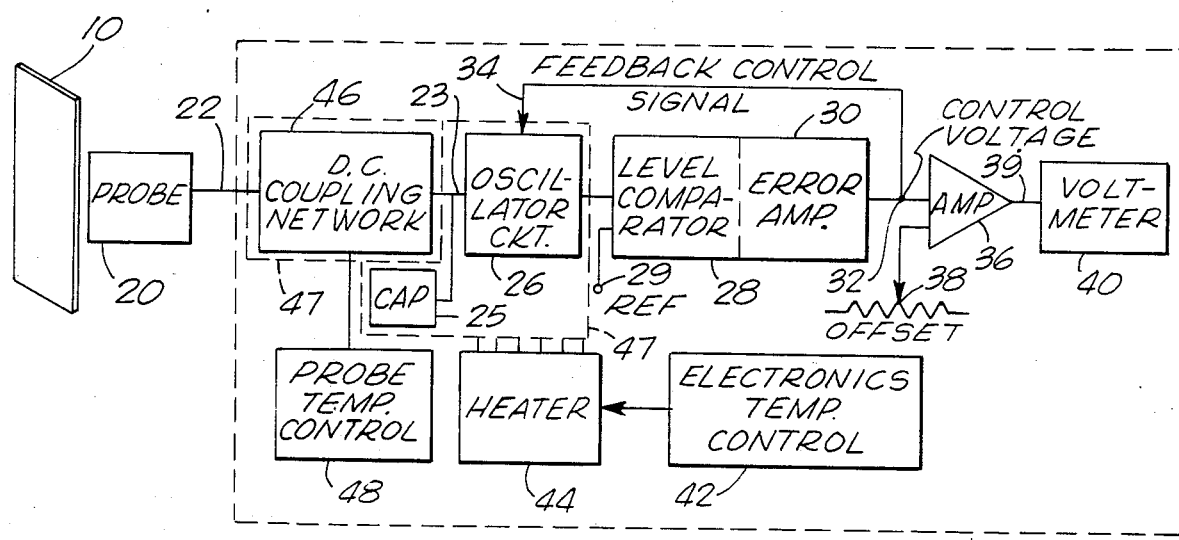
FIG. 4 is a block diagram of the meter of the present invention showing the probe connected to circuitry of an electronic package.

With reference to FIG. 4, the probe 20 is connected by a coaxial cable 22 to an electronic package 24. The probe 20 includes an inductive element for a tank circuit, described more fully below. A capacitive element for the tank circuit is a tank capacitor 25 located within the electronic package. An oscillator circuit 26 having an oscillator output 27 is conected to the probe 20 together with the tank capacitor 25 at a tank node 23.

Preferably the oscillator circuit 26 is a high frequency operational amplifier circuit having optically coupled gain control for controlling the voltage amplitude of oscillation. The tank node 23 can be connected with positive feedback in the operational amplifier circuit to a non-inverting input of an operational amplifier. Optically coupled gain voltage amplitude control of operational amplifier circuits are known in the prior art. For example, a Raytheon CK 2142 optically controlled variable resistor can be used as a gain control element for the operational amplifier circuit.

A level comparator 28 compares the voltage at the oscillator output 27 with a reference voltge 29. The level comparator 28 is connected to drive an error amplifier 30 to produce a control voltage 32. The control voltage 32 is connected as a filtered feedback control signal 34 optically coupled to the oscillator circuit 26 for controlling the gain of the oscillator circuit 26 to stabilize the voltage at the oscillator output 27. The control voltage 32 can be nominally 6.5 volts.

The magnitude of the control voltage 32 required to sustain oscillation is an inverse function of the Q of the tank circuit. The control voltage 32 is also directly related to the loading effect imposed on the inductive element of the probe by eddy currents induced in a lossy conductive surface placed in the field of the probe. Ignoring certain non-linearities inherent in the electronics implementation, the net result is a control voltage 32 which is a linear function of the conductance per unit square (Gs) of the conductive surface.

Preferably the tank capacitor 25 is adjustable for tuning the resonant frequency of the tank circuit to the frequency of maximum Q of the tank coil 64.

An output amplifier 36, balanced by an offset potentiometer 38, is driven by the control voltage 32 for producing an output voltage 39 which is read by a voltmeter 40.

Temperature Control

The electronic package 24 is equipped with an electronic temperature control 42 connected to a heater 44 for stabilizing the temperature of circuitry within the electronic package 24, thereby reducing variations in the output voltage 39 caused by thermal drift of the circuitry.

The electronic package 24 also provides temperature control of the probe 20 to prevent changes in the Q of the inductive element of the probe 20 which would otherwise result from changes in probe inductive element resistance as a function of temperature. A DC coupling network 46 is connected in series between the probe 20 and the tank node 23 for superimposing heat-producing direct current on the inductive element of the probe 20. A probe temperature control 48 is connected to the DC coupling network 46 to control the magnitude of the direct current within the probe 20 for stabilizing the temperature of the inductive element.

The oscillator circuit 26, the tank capacitor 25, and the DC coupling network 46 of the electronic package 24 can be enclosed in a thermal shield 47, the thermal shield 47 being thermally coupled to the heater 44. The thermal shield 47 can have separate cavities, one enclosing the oscillator circuit 26 and the tank capacitor 25, the other enclosing the DC coupling network 46. Thus the temperature stabilization by the electronic temperature control 42 is concentrated where it is most needed.

Figure 5:
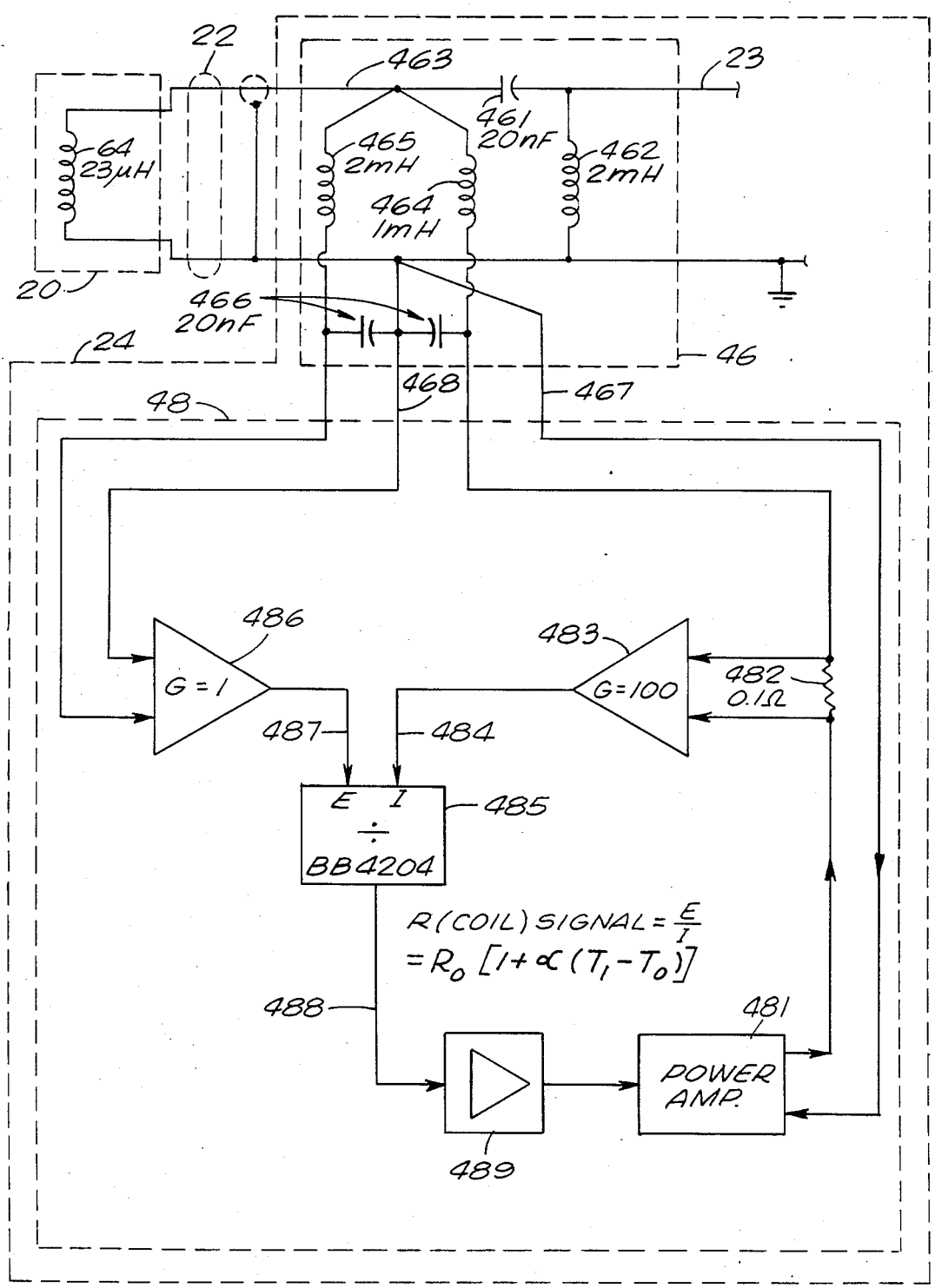
FIG. 5 is a fragmentary simplified schematic diagram of the meter of FIG. 4 showing a D.C. coupling network and a probe temperature control in the electronic package.

With reference to FIG. 5, the DC coupling network 46 includes a coupling capacitor 461 and a grounded bypass inductor 462 connected to the tank node 23 for coupling the tank node 23 to a coupler output 463, the coupler output 463 being connected by the coaxial cable 22 to the probe 20.

The coupler output 463 is coupled to the probe temperature control 48 by a current inductor 464 and a sensing inductor 465, each having a grounded bypass capacitor 466 for blocking signals at the oscillator frequency. A grounded power return 467 and a grounded voltage return 468 separately reference the probe temperature control 48 to the DC coupling network 46.

The probe temperature control 48 has a power amplifier 481, referenced to the power return 467, for driving the power inductor 464 through a shunt resistor 482. Direct current from the power amplifier 481 is coupled to the probe 20 by the current inductor 464, producing a proportional voltage across the shunt resistor 482. A current sensing amplifier 483 is connected across the shunt resistor 482 for providing a current signal 484 to an analog divider circuit 485. A voltage sensing amplifier 486 is connected to the sensing inductor 465 and the voltage return 468 for providing a voltage signal 487 to the analog divider circuit 485. The analog divider circuit 485 is connected for providing a resistance signal 488 proportional to the resistance of the probe 20 by dividing the voltage signal 487 by the current signal 484. The resistance signal 488 is processed by a control amplifier 489 for driving the power amplifier 481 so that current coupled to the probe 20 is reduced by any increase in the resistance signal 488, stabilizing the temperature and resistance of the probe 20.

The control amplifier 489 has an adjustable temperature set point and proportional, integral and derivative (PID) control modes for dynamic compensation.

Preferably the power amplifier 481 can provide from approximately 0.1 to 1.5 amperes DC to the probe 20 for temperature control. The current minimum provides for continuous resistance monitoring while the maximum provides circuit protection and limits the required dynamic range of control.

In summary of the above, the probe temperature control 48 controls the temperature of the tank coil in the probe 20 by reacting to changes in the resistance of the tank coil, the resistance being a function of temperature, the apparatus superimposing a variable direct current on the tank coil for correspondingly heating the tank coil as required for keeping the resistance (and temperature) essentially constant. The resistance signal 488, being proportional to the resistance of the probe 20 (including the tank coil), is thus indicative of the temperature of the probe 20. Accordingly, the resistance signal 488, after processing by the control amplifier 489, drives the power amplifier 481 for controlling the magnitude of the direct current that passes from the power amplifier 481 through the shunt resistor 482 and into the probe 20 by way of the DC coupling network 46.

The inductor 465, in cooperation with its associated grounded bypass capacitor 466, acts as a low-pass filter for blocking signals at the oscillator frequency, permitting the sensing amplifier 486 to produce the voltage signal 487 as being primarily representative of the voltage provided to the probe 20 at the coupler output 463, with the AC component from the tank node 23 substantially removed or diminished by the blocking of the oscillator frequency. Thus the voltage signal 487 is predominantly representative of an offset voltage in the probe 20 that is produced by the direct current that is coupled thereto through the current inductor 464 from the shunt resistor 482.

The source for the direct current that is produced by the power amplifier 481 is an appropriate power connection from a suitable source of direct current such as a fixed voltage DC power supply (not ehown) to the power amplifier 481. The detailed operation of the power amplifier 481 is not critical since it can be characterized as a voltage amplifier, a current amplifier, or both; as long as the power to the shunt resistor 482 is responsive to the signal that is produced by the control amplifier 489. This is because the resistance signal 488 is responsive to the current signal 484 that is in turn directly representative of the current in the shunt resistor 482, so that the control amplifier 489 cooperates with the power amplifier 481 for producing an appropriate magnitude of the variable direct current through the shunt resistor 482 to the probe 20 to restore a desired magnitude of the resistance signal 488 whenever the temperature of the probe 20 deviates from a corresponding desired temperature. The variations in the direct current produce immediate corresponding changes in both the current signal 484 and the voltage signal 487, but in the same ratio, so that the resistance signal 488 does not change appreciably until the corresponding change in the direct current in the probe 20 causes a change in the temperature of the probe 20. Then, because the resistance of the probe changes with this chang in temperature, there is a further change in the voltage signal 487 (because, at a given current level, the voltage drop across the probe 20 changes with its resistance), this change being toward the desired magnitude of the resistance signal 488. The operation of this closed-loop can be refined by appropriately selecting the dynamic compensation of the control amplifier 489 according to conventional control system methodology.

Probe Constitution

Figure 2:
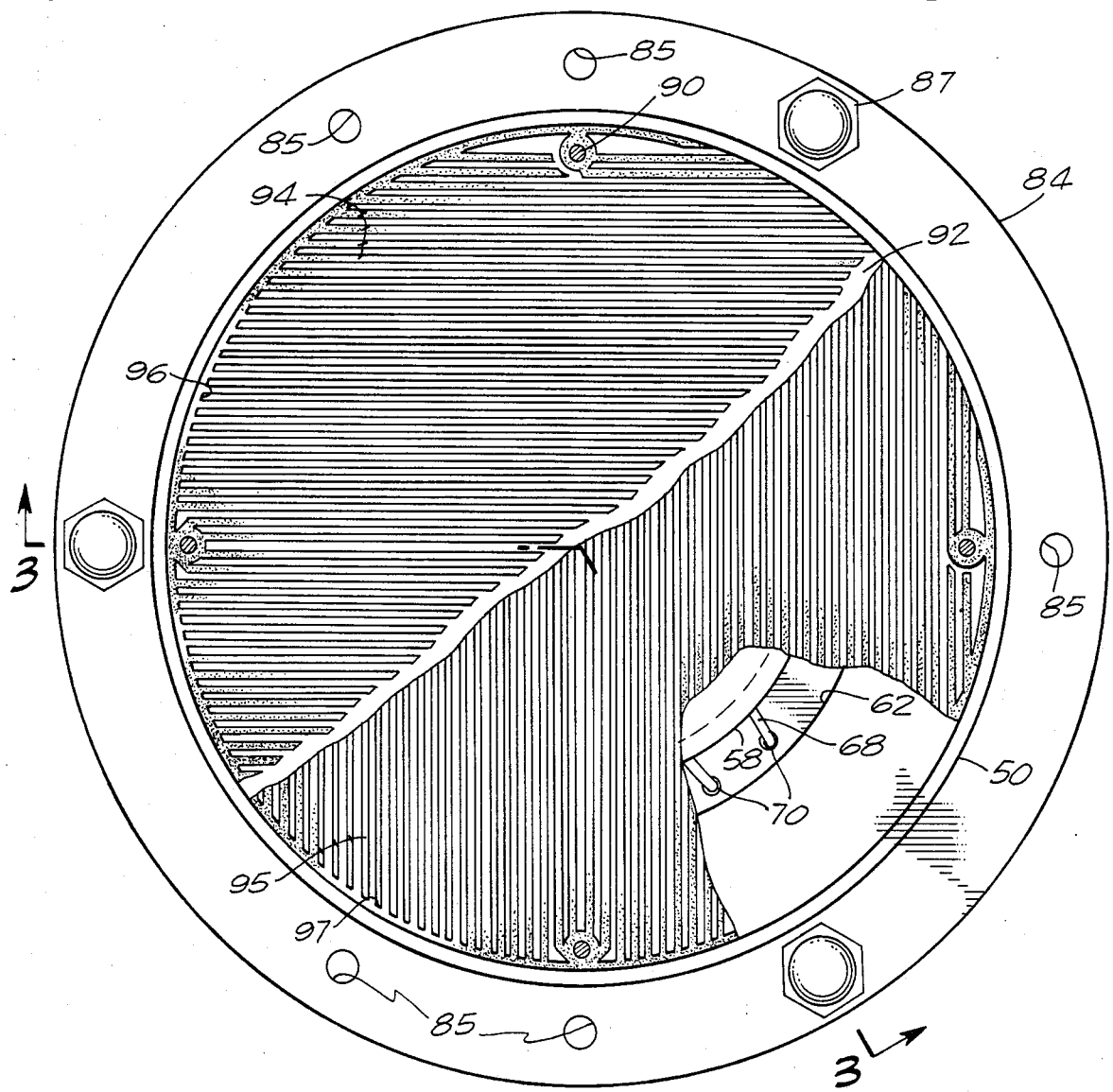
FIG. 2 is a fragmentary plan view of the probe taken along line 2—2 in FIG. 1.
Figure 3:
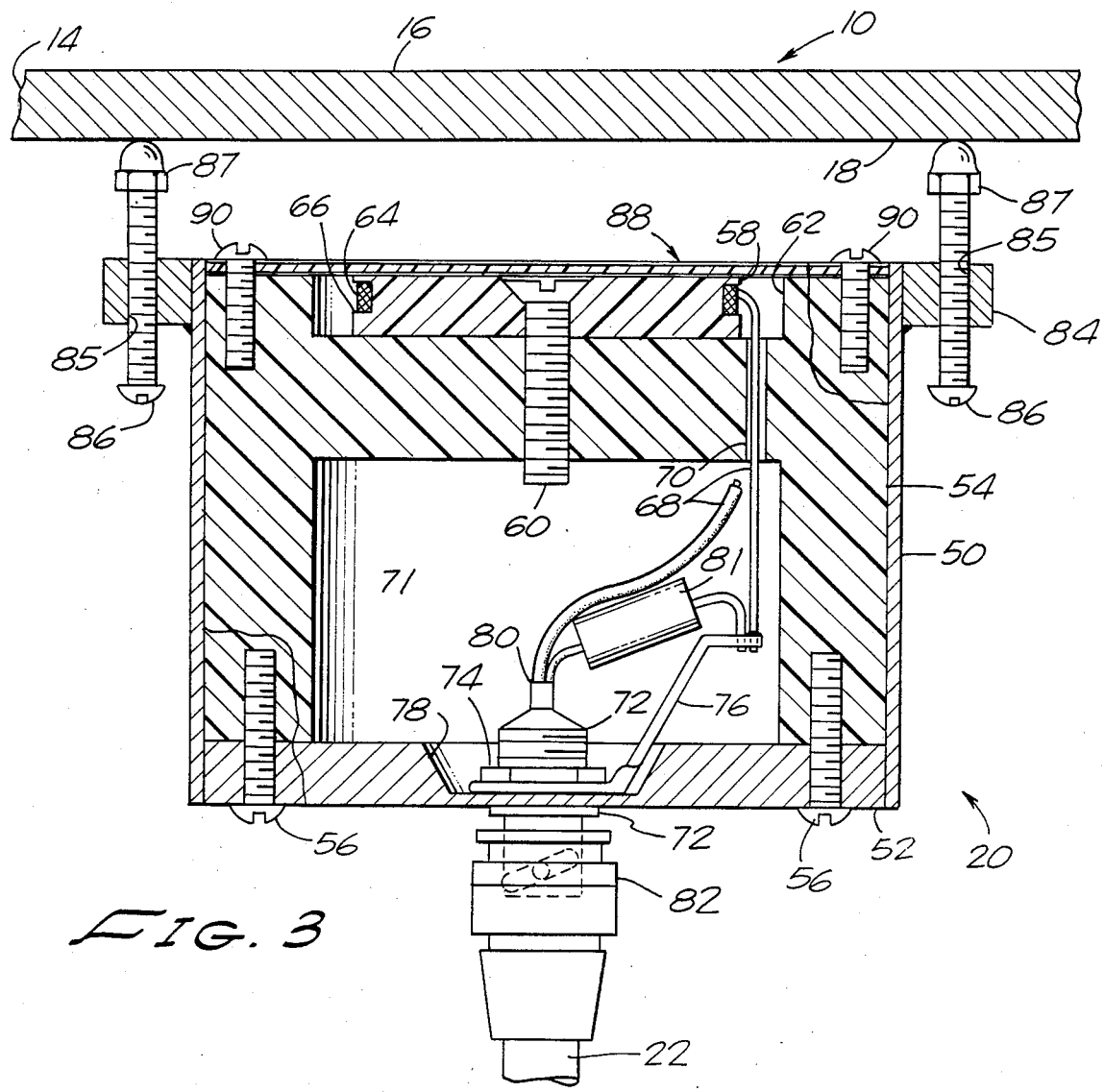
FIG. 3 is a sectional elevational view of the probe taken along the line 3—3 in FIG. 2.

With reference to FIGS. 2 and 3, a housing cylinder 50 having its axis perpendicular to the sample 10 is closed at the end farthest from the sample 10 by a housing disk 52, the housing disk 52 being pressed into the housing cylinder 50. A coil support 54 is fastened within the housing cylinder 50 against the housing disk 52 by at least one support screw 56. A coil form 58 is fastened to the coil support 54 by a form screw 60, the coil form 58 being located flush within a coil cavity 62 in the coil support 54 opposite the housing disk 52. The coil support 54 and the coil form 58 can be made from a low magnetic permeability, non-conductive material having low dielectric loss characteristics at the operating frequency, such as an acetal resin. The coil form screw 60 can be made from a low magnetic permeability non-conductive material having low dielectric loss characteristics at the operating frequency, such as Nylon.

The inductive element of the probe 20 is a tank coil 64 wound within a groove 66 on the coil form 58, with the axis of the tank coil 64 preferably concentric with the housing cylinder 50. Each end lead 68 of the coil 64 passes through a passage 70 in the coil support 54 into a junction cavity 71 in the coil support 54.

A coaxial receptacle 72 protrudes the housing disk 52 and is fastened thereto by a receptacle nut 74, the nut 74 also securing a lug 76 within the junction cavity 71. A receptacle counterbore 78 in the housing disk 52 provides proper mounting thickness for the coaxial receptacle 72. The end leads 68 of the coil 64 are connected one to the lug 76, the other to an inner conductor 80 of the receptacle 72. The coaxial cable 22 is connected to the receptacle 72 by a coaxial plug 82 so that the tank coil 64 is connected across a shield and inner conductor of the coaxial cable 22 for connection to the electronic unit 24 as described above. The coaxial cable 22 can be about three feet (1 meter) long for convenient manipulation of the probe 20.

Preferably an auxiliary capacitor 81 that can have a mica dielectric is connected between the inner conducter 80 and the lug 76 across the tank coil 64 to suppress parasitics associated with the coaxial cable 22. The capacitance of the tank circuit comprises the tank capacitor 25, the auxiliary capacitor 81, and capacitance of the coaxial cable 22, the tank capacitor 25 being the dominant capacitance.

Preferably the Q of the tank coil 64 is high over a relatively broad range of frequencies so that the adjustment of the resonant frequency of the tank circuit is not critical. The tank coil 64 comprises 16 turns of wire wound over a 1.5 inch (38 mm) root diameter of the groove 66 to obtain an inductance of 23 microhenries with a Q in excess of 95 at oscillator frequencies between 2.5 and 3.25 megahertz and a maximum of about 97 at frequencies between 2.8 and 3 megahertz.

A housing flange 84 is fixed externally to the housing cylinder 50 opposite to the housing disk 52. The housing flange 84 is provided with at least three threaded holes 85 equidistant from the axis of the tank coil 64. At least three spacer screws 86, each capped with an acorn nut 87, engage appropriate ones of the threaded holes 85 for locating the probe 20 an adjustable distance from the sample 10. The spacer screws 86 and the acorn nuts 87 can be made from a low permeability, non-conducting material such as Nylon. The spacer screws 86 can be adjusted to align the axis of the tank coil 64 perpendicular to the sample 10 at a predetermined distance from the conducting surface 16 when the acorn nuts 87 are held against the supporting surface 18. For curved samples, perpendicularity is measured on the axis of the tank coil 64. It should be understood that the predetermined distance is an effective distance from the conducting surface 16 of curved samples.

A complement of three of the spacer screws 86, as shown in FIG. 2, is appropriate for use with flat and spherically curved samples. A rectangular or square complement of four of the spacer screws 86 is appropriate for use with flat and cylindrically curved samples.

Alternatively, a single internally threaded cylinder engaging screw threads on the housing flange 84 can be used in place of the spacer screws 86 and the acorn nuts 87 for adjustment of the distance between the tank coil 64 and the supporting surface 18. Additionally, interchangeable, fixed length spacers could be fastened to the housing flange 84, each spacer corresponding to a specific thickness of the sample 10.

Probe Shielding

Preferably the housing cylinder 50, the housing disk 52, and the housing flange 84 are made of a conducting material such as aluminum for providing electromagnetic shielding of the portion of the magnetic field associated with the tank coil 64 not directed toward the sample 10. In a preferred version, the housing cylinder is about 3 inches (76 mm) in diameter.

Preferably a shield member 88 covering the tank coil 64 and the coil support 54 is fastened to the coil support 54 by a shield screw 90. The shield member 88 comprises a shield support 92 made from a suitable nonconducting material of low magnetic permeability having low dielectric loss characteristics at the operating frequency. The shield support 92 is provided on one side with a closely spaced array of narrow first parallel conductors 94, the first parallel conductors 94 being interconnected on one end only by a first finger interconnection 96 for electrostatic shielding of the tank coil 64 from the sample 10 with minimal eddy current magnetic loading of the tank coil 64.

Preferably the shield support 92 is provided with a closely spaced array of narrow second parallel conductors 95 interconnected on one end only by a second finger interconnection 97. The first interconnection 96 and the second interconnection 97 of the shield member 88 are electrically connected to the housing cylinder 50 and the housing disk 52, completing electrostatic shield enclosure of the tank coil 64. The first parallel conductors 94 and the second parallel conductors 95 are on opposite sides of the shield support 92 and oriented to form an intersecting pattern, improving the electrostatic shielding between the tank coil 64 and the sample 10. The arrangement of parallel conductors on the shield member 88 provides effective electrostatic shielding for the tank coil 64 without interfering with magnetic coupling between the tank coil 64 and the sample 10. In the drawings, the first parallel conductors 94 and the second parallel conductors 95 are straight, crossing at 90 degrees. However, curved conductors and other crossing angles can also be used.

The meter can be used for measuring sheet conductance without requiring the tank coil 64 to be immediately pooximate to the conductive surface 16. The meter can be used effectively with the tank coil 64 located more than 0.150 inch from the conductive surface 16. In fact, the tank coil 64 can be 0.75 inch or more from the conductive surface 16. The conductive surface can be a deep lamination in the sample or a delicate coating on one side of a thick sample having unrestricted area, the delicate coating not being touched by the meter.

The meter of the present invention has been tested in a preliminary version not incorporating the DC coupling network 46 and the probe temperature control 48. The tests were performed with the probe 20 located 0.75 inch (19 mm) from the conducting surface 16 of the sample 10. The indicated sheet resistance $R_s$ has been shown to be unaffected by the size of the sample in the range of from about 8 inches (20 cm) square to above 24 inches (61 cm) square. Reducing the sample size to 6 by 4 inches (15 by 10 cm) increases the indicated $R_s$ by less than 5%. There is no limit to the largest dimension of the sample. Large samples have no effect on the accuracy of measurement.

The meter was calibrated to obtain 10 volts at the output voltge 39 while measuring no sample ($G_s=0$) and $-2.5$ volts while measuring a sample 10 having a $G_s$ of approximately 0.33 Siemens per square ($R_s=3$ ohms per square). In terms of the output voltage 39, the indicated sheet conductance of the sample 10 is $G_s=0.0265$ (10-B) Siemens per square where V is the output voltage 39. The preliminary test results indicate that the meter can provide $\pm 1.8\%$ repeatability and $\pm 4.7\%$ linearity at a 3 sigma confidence level over a sheet conductivity range of from 0.09 to 0.36 Siemens per square.

Preferably the voltmeter 40 is adapted with additional circuitry to provide a direct reading of $G_s$ and/or $R_s$ by scaling, offset and/or electronic analog/digital computation means known in the prior art.

Although the present invention has been described in considerable detail with reference to certain preferred versions thereof, other versions are possible. For example, the housing cylinder 50, the housing disk 52 and the housing flange 84 can be a single unit. Also, the tank coil 64 and housing diameter can be made larger to provide increased sensitivity at extended spacings from the conductive surface, or, made smaller to provide a smaller effective area of measurement at the conductive surface. Also, the measurement range can be varied by scaling, offset, and sensitivity adjustment means known in prior art. Also, the meter can be located against a conductive surface of the sample if the conductive surface is not too delicate to be touched by the meter. Therefore, the spirit and scope of the appended claims should not necessarily be limited to the description of the versions contained herein.

What is claimed is:

1. A method for measuring conductance of a sample comprising the steps of:
   (a) selecting apparatus comprising:
      (i) a resonant tank circuit having a tank coil for loading by the sample;
      (ii) an oscillator incorporating the tank circuit;
      (iii) a control circuit for the oscillator responsive to the loading of the tank coil by the sample, the control circuit producing a control signal proportional to the loading; and
      (iv) means responsive to the control signal for indicating the sheet conductance;
   (b) coupling a variable direct current to the tank coil;
   (c) measuring the magnitude of the direct current;
   (d) measuring an offset voltage produced in the tank coil by the direct current;
   (e) dividing the measured offst voltage by the measured direct current for producing a resistance signal representing the resistance of the tank coil;
   (f) controlling the direct current in response to the resistance signal for stabilizing the temperature of the tank coil;
   (g) positioning the tank coil in a predetermined relation to the sample; and
   (h) reading the sheet conductance from the indicating means.

2. Apparatus capable of measuring sheet conductance of a sample having unrestricted area and having a conducting surface and a supporting surface parallel to the conducting surface, the supporting surface being more than 0.15 inch from the conducting surface, the apparatus not touching the conducting surface, the apparatus comprising:
   (a) a probe comprising:
      (i) a tank coil in a resonant tank circuit, the tank coil having an axis;
      (ii) means for locating the probe against the supporting surface of the sample with the axis of the tank coil perpendicular to the sample and a predetermined distance between the tank coil and the sample;
      (iii) a conductive housing for the tank coil, the conductive housing being open at one end proximate the sample, the conductive housing shielding magnetic flux associated with the tank coil not directed toward the sample; and
      (iv) a shield for preventing capacitive coupling between the tank coil and the sample, the shield comprising a plurality of separate, elongated narrow conductors on opposite sides of an insulating substrate covering the open end of the housing, the conductors crossing to form an intersecting pattern, the conductors being electrically connected to the housing at one location only on each conductor for preventing eddy current losses in the shield, for providing an electrostatic shield enclosing the coil;

(b) an oscillator incorporating the tank circuit in resonance, the oscillator further comprising a high frequency operational amplifier having optically coupled gain for external control;

(c) means for controlling the temperature of the tank coil by varying a direct current added to the tank coil in response to changes in measured resistance of the tank coil, the controlling means comprising:
  (i) a DC coupling network for adding the direct current to the tank coil, the network having a coupler output connected to the tank coil, the network incorporating a circuit for sensing an offset voltage at the coupler output, the offset voltage resulting from the direct current in the tank coil, the sensing circuit including means for blocking oscillator signals;
  (ii) a power amplifier for variably producing the direct current in response to an external signal;
  (iii) meane for measuring the magnitude of the direct current; and
  (iv) a circuit for producing the external signal for the power amplifier as a quotient proportional to the offset voltage divided by the magnitude of the direct current, the external signal being indicative of the measured resistance, the direct current being reduced in response to increased resistance of the tank coil;

(d) a control circuit for the oscillator responsive to loading of the tank coil by the conducting surface, the control circuit stabilizing the amplitude of oscillation of the oscillator and producing a control signal proportional to the loading; and (e) means responsive to the control signal for indicating the sheet conductance.

3. Apparatus for measuring conductance of a sample comprising:
  (a) a resonant tank circuit having a tank coil for loading by the sample, the tank coil having an axis;
  (b) means for positioning the tank coil in a predetermined relation to the sample;
  (c) an oscillator incorporating the tank circuit;
  (d) a control circuit for the oscillator responsive to the loading of the tank coil by the sample, the control circuit stabilizing the amplitude of oscillation of the oscillator and producing a control signal proportional to the loading;
  (e) means for controlling the temperature of the tank coil by coupling a variable direct current into the tank coil, the direct current varying in response to a circuit for measuring the resistance of the tank coil so that the direct current is reduced when the resistance of the tank coil increases; and
  (f) means responsive to the control signal for indicating the conductance.

4. The apparatus of claim 3 wherein the means for controlling the temperature comprises:
  (a) a D.C. coupling network for adding the direct current to the tank coil, the coupling network being connected in the tank circuit;
  (b) a power amplifier for variably producing the direct current in response to a resistance signal, the power amplifier being connected to the coupling network;
  (c) means for measuring a voltage offset in the tank coil in response to the direct current;
  (d) means for measuring the magnitude of the direct current; and
  (e) means for producing the resistance signal as a quotient proportional to the voltage offset divided by the direct current.

5. The apparatus of claim 4 in which the measuring means comprises a low-pass filter in the D.C. coupling network, the filter having an output connected to an input of a voltage amplifier, the voltage amplifier driving the producing means, and the current measuring means comprises a current-shunt resistor connected between the power amplifier and the coupling network, opposite ends of the current-shunt resistor being connected to corresponding inputs of a sensing amplifier, the sensing amplifier having an output connected to the producing means.

6. The apparatus of claim 3 further comprising a shield for preventing capacitive coupling between the tank coil and the sample, the shield being located in fixed relation to the tank coil and comprising a plurality of separate elongated narrow conductors, the conductors being electrically interconnected only at one location on each conductor for preventing eddy current losses in the shield.

7. The apparatus of claim 6 wherein the control circuit is in an electronics unit and the tank coil, the shield and the positioning means are in a probe remote from the electronics unit for convenient manipulation of the tank coil.

8. The apparatus of claim 7 wherein the probe is connected to the electronics unit by a coaxial cable more than about two feet long.

9. The apparatus of claim 3 wherein the oscillator further comprises a high frequency operational amplifier circuit having optically coupled gain control driven by the control signal.

10. The apparatus of claim 6 further comprising a conductive housing for the tank coil, the conductive housing being open at one end proximate to the sample, the conductive housing shielding magnetic flux associated with the tank coil not directed toward the sample, the open end of the housing being covered by the shield for preventing capacitive coupling, the interconnection of the conductors being electrically connected to the conductive housing for providing an electrostatic shield enclosing the coil.

11. The apparatus of claim 10 wherein the conductors of the shield for preventing capacitive coupling form at least two closely spaced surfaces, the conductors of the respective surfaces being oriented to form an intersecting pattern on opposite sides of an insulating substrate.

* * * * *